US006274154B1

(12) United States Patent
Chou

(10) Patent No.: US 6,274,154 B1
(45) Date of Patent: Aug. 14, 2001

(54) ALOE VERA GLOVE AND MANUFACTURING METHOD

(76) Inventor: Belle L Chou, 2845 Whipple Rd., Union City, CA (US) 94587

( * ) Notice: Subject to any disclaimer, the term of this patent is extended or adjusted under 35 U.S.C. 154(b) by 0 days.

(21) Appl. No.: 09/288,067

(22) Filed: Apr. 7, 1999

(51) Int. Cl.$^7$ ............................. A01N 25/34; A41D 19/00
(52) U.S. Cl. ................................ 424/402; 2/158; 2/159; 2/161.7; 2/168; 2/169
(58) Field of Search .................................... 424/402, 443; 2/159, 158, 161.7, 168, 169; 15/227

(56) References Cited

U.S. PATENT DOCUMENTS

| 4,122,554 | 10/1978 | Stager | 2/164 |
| 4,185,330 | 1/1980 | Stager | 2/164 |
| 4,186,445 | 2/1980 | Stager | 2/164 |
| 4,775,372 | * 10/1988 | Wilberg . | |
| 5,417,968 | 5/1995 | Staats | 424/78.07 |
| 5,614,202 | 3/1997 | DeFina | 424/402 |
| 5,682,617 | 11/1997 | Tumas | 2/239 |
| 5,869,072 | 2/1999 | Berry | 424/402 |
| 5,910,567 | * 6/1999 | Tanaka et al. . | |

FOREIGN PATENT DOCUMENTS

JP09002962 A * 1/1997 (JP) .
94/12115 * 6/1994 (WO) .

* cited by examiner

Primary Examiner—Thurman K. Page
Assistant Examiner—Brian K. Seidlech
(74) Attorney, Agent, or Firm—Intellectual Property Law Group; Otto O. Lee; C. George Yu

(57) ABSTRACT

A moisturizing and therapeutic glove is disclosed which includes a thin layer of Aloe Vera coated evenly and uniformly on an inside surface of the glove. Aloe Vera is attached to the surface through a dehydration process achieved with a controlled drying method. Aloe Vera soothes hand during the wearing of the glove.

12 Claims, 1 Drawing Sheet

ALOE VERA GLOVE AND MANUFACTURING METHOD

BACKGROUND

This invention relates generally to hand care products, and specifically relates to applying Aloe Vera on the inner surface of disposable gloves to protect and soothe the hands during and after application of disposable gloves.

Disposable gloves are widely used as a protective measure to insulate hands from the objects handled by the wearer of gloves. To allow ease in handling objects, disposable gloves are made of thin and elastic material to minimize the space between the skin and the glove. Due to poor air circulation resulting from tight insulation, hand sweating is a common problem among glove wearers. Prolonged wearing of disposable gloves causes a moist environment on the surface of the hand that allows viruses, bacteria, yeast and fungus to grow and multiply. Itchiness is a frequent result of wearing disposable examination gloves for extended periods.

Powders are commonly used on the inner surface of gloves to alleviate sweating and to make donning, wearing and removal of gloves easier. However, continuous sweating can easily overwhelm the thin layer of powder that is commonly attached to the surface of the glove. This is especially the case when continuous and frequent wearing of gloves is required. For example, dentists may continuously wear gloves during a dental surgical procedure for up to 40 minutes. In addition, hand washing is necessary after the use of powdered gloves. Frequent hand washing to remove powders may also cause excess dryness of the skin.

The need for disposable gloves that can prevent adverse side effects caused by extensive use is apparent. Various patents disclose different types of gloves that contain lotions. During glove use the lotions come into contact human skin and condition the skins. For example, U.S. Pat. No. 5,614,202 discloses a moisturizing glove that contains a middle layer saturated with lotion. The porous inner layer allows the lotion to pass through and contact the skin. U.S. Pat. Nos. 4,186,445 and 4,185,330 disclose gloves that have inner lining made of a lotion absorbent material. By impregnating the lotion onto the absorbent material, the lotion can condition the hands during application of the gloves.

A common feature of the above disclosures is the use of multiple layers in the glove design. Compared to single layer disposable gloves, the complex design of multiple layer gloves makes production far more costly. Most importantly, the thickness of the layers and the complicated structures of the gloves hinder hand flexibility when the glove wearer tries to pick up and manipulate objects. Such multiple layer designs are suitable for moisturizing hands, but are not suitable for manipulating objects, especially for professions that require handling of fine tasks with precision.

Disposable gloves are generally made of three types of materials: natural rubber latex, acrylonitrile, and polyvinyl chloride. Natural rubber latex is sensitive to oil-based substances. Prolonged contact between latex and oil-based substance can adversely affect durability and flexibility of the latex material. Most commercially available lotions contain oil-based substances. The use of lotions in prior arts will substantially shorten the shelf life of a natural rubber glove.

There is therefore a need for low cost disposable gloves that can apply moisturizing and therapeutic substances to the hands during the glove use without leaving a greasy feel or look to the skin, while at the same time, retain the characteristics and functions of conventional single layer gloves.

SUMMARY

The present invention satisfies these needs. This invention is a novel disposable glove with Aloe Vera uniformly applied to the inner surface of the glove through a dehydration process, and a method for making such a glove.

One object of this invention is to condition and soothe the hands during glove use.

Another object of this invention is to produce a glove that is equivalent to a single layer glove in the user's ability to pick up and manipulate objects.

Still another object of this invention is to prevent growth of bacteria, viruses, yeast and fungi on the hands, which become more active in a wet environment resulting from sweating during prolonged or frequent wearing of gloves.

A related object is to cause the anti-microbial substance to dissociate and release from the glove surface in response to the degree of wetness of hand.

A further object is to preserve the shelf life of glove by using natural non-oil based substance and to preserve the activity of the therapeutic substance by keeping the substance in a dehydrated state.

The above objects are accomplished by applying Aloe Vera evenly to the inner surface of a disposable examination glove through dehydration.

The objects are further accomplished by a method of manufacturing the Aloe Vera glove. The disposable gloves are first treated with chlorine solution to wash off any powders, extract soluble substances in the composite material, and kill microorganisms. After drying, the gloves are turned inside out and dipped into a prepared Aloe Vera solution to saturate the outer surface. The gloves are then dried in a tumbling heater within a controlled narrow range of temperature between 45° C. and 65° C., and for a specific length of time. This causes water to evaporate and the Aloe Vera to evenly coat the glove surface. After cooling to room temperature, the gloves are inverted so that the side with Aloe Vera coating is facing inside.

DETAILED DESCRIPTION OF THE INVENTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
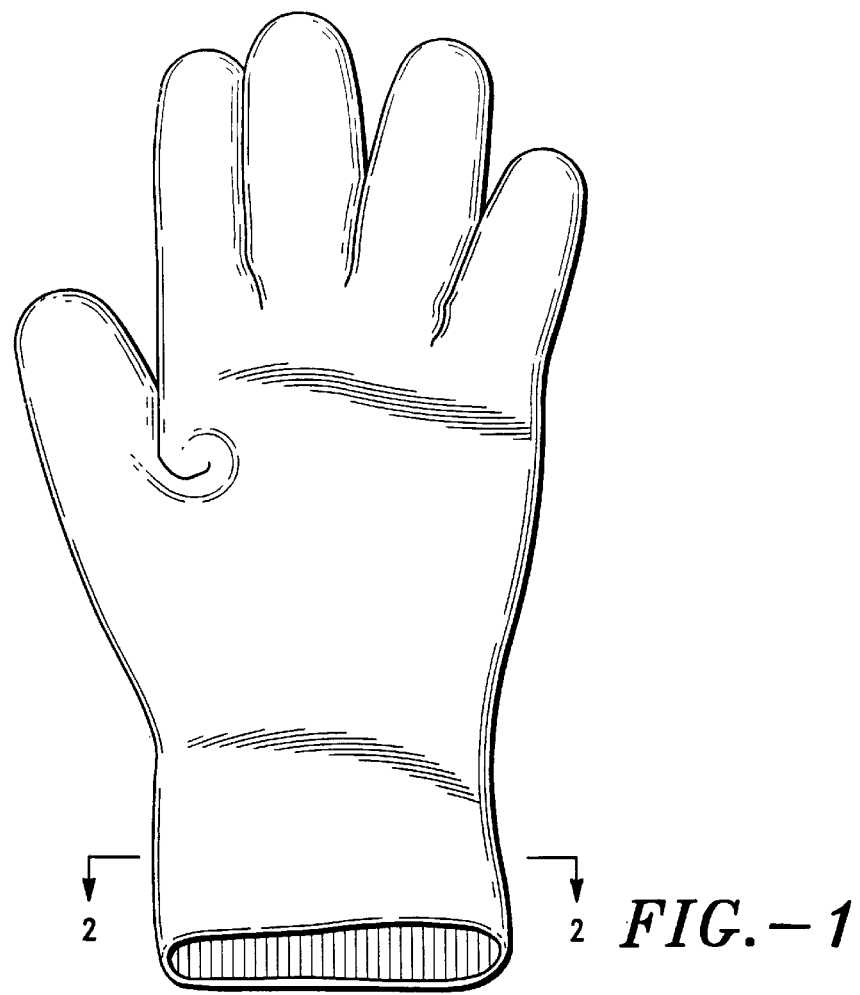
FIG. 1 is the front perspective view of a Aloe Vera glove constructed in accordance with the principles of the present invention.
Figure 2:
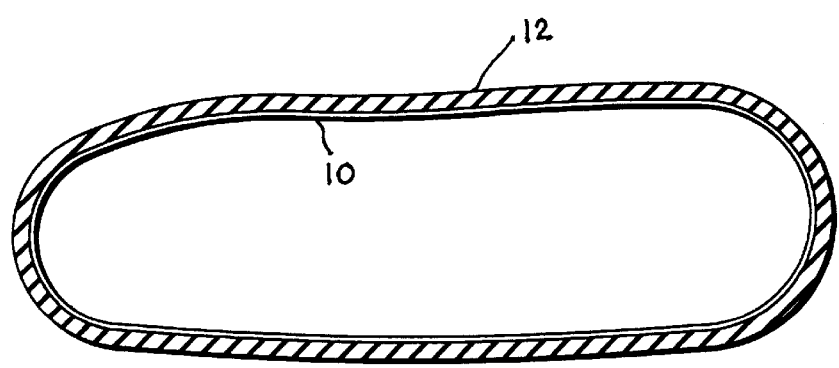
FIG. 2 is a sectional view taken along the lines 2—2 of FIG. 1.

The invention is a disposable glove as illustrated in FIG. 1, which has Aloe Vera 10 evenly coated on the inner surface in a dehydrated state, as illustrated in FIG. 2. The glove retains the features of a disposable examination glove, which is simple and convenient to use and allows the wearer to handle fine tasks with precision. The invention also discloses a manufacturing method for modifying a disposable glove by coating Aloe Vera on the inner surface of the glove. The glove is coated with Aloe Vera 10 through dehydration that is accomplished by a well-controlled heating process.

A disposable glove is made of various materials to form a layer 12. Resinous materials such as vinyl or polymer materials such as acrylonitrile are common choices. Three commonly used materials for making disposable gloves are natural rubber latex, acrylonitrile and polyvinyl chloride.

In one preferred embodiment, the glove is made of natural rubber latex. Since natural rubber latex is sensitive to oil-based substances, gloves made of natural rubber latex should not be exposed to oil-based substances. In this invention, Aloe Vera is used to coat the gloves and it does not contain any detectable oil-based substances. Coating gloves with Aloe Vera does not affect the glove's shelf life. In another preferred embodiment the glove is made of acrylonitrile polymer.

Aloe Vera is a natural plant extract that has a long history of folk medicine usage. Aloe Vera has been used for external treatment of wounds, burns and skin irritations, and internal treatment of various conditions. Aloe Vera is a popular ingredient in skin-care products. It is also a powerful anti-inflammatory and anti-microbial agent. Aloe Vera is soluble in water and contains non-detectable oil content.

Aloe Vera glove retains the characteristic of a disposable glove without any visible modification, and is easy and convenient to use. The affiliation between Aloe Vera and the glove surface is through a force provided by dehydration. Such affiliation is loosened when sweat dissolves Aloe Vera. The longer a glove is worn, the more likely the hand will sweat, and consequently more Aloe Vera will be dissolved and disassociated from the glove surface, and be applied to hand. The active ingredients in Aloe Vera can then condition hand skin and prevent microorganisms from growing under the wet condition.

In one preferred embodiment, 100% Aloe Vera gel is used to coat the gloves. Aloe Vera is evenly and uniformly distributed on the inner surface of the glove at a thickness of about 0.01 millimeter. The association between Aloe Vera and the surface is achieved by a non-covalent force provided through dehydration.

The method of manufacturing gloves involves treating a commercially available disposable glove to eliminate residue powders, soluble substances, and microorganisms, turning the glove inside out, dipping it into an Aloe Vera solution and heating the glove to cause water to evaporate.

A glove is preferably first treated with a chlorine solution or chlorine gas. Chlorine solution can help to sterilize the gloves, to wash off powders, and most importantly for natural latex gloves, to dissolve residual proteins that could potentially trigger severe allergic reactions among repeat users. After the outside surface of the glove is treated with the chlorine solution, it is turned inside out, and the glove is again treated with the chlorine solution. The residue chlorine is neutralized by using ammonia and the gloves are then dried.

An Aloe Vera solution will then be prepared. One hundred percent concentrated Aloe Vera gel is dissolved in distilled water to generate an Aloe Vera solution. The preferred concentration of the solution is about 20%. To associate Aloe Vera with the surface of the glove, Aloe Vera solution can be sprayed onto the surface of the glove. Alternatively, the glove can be immersed into the Aloe Vera solution. The latter method is preferred because it creates a complete and even distribution of the Aloe Vera solution.

In one preferred embodiment, the dipping process is accomplished by grouping a number of gloves in a batch to achieve higher manufacturing efficiency. The gloves are immersed in the solution for at least 10 minutes to allow adequate absorbency.

Aloe Vera is attached to the surface of the glove through a controlled dehydration process. The water in the Aloe Vera solution is caused to evaporate through heating. Although a higher temperature will cause water to evaporate quicker, excess heat may damage the gloves. For example, gloves exposed to excessive heat of over 70° C. may turn brownish and become brittle. To shorten the heat exposure time, a heating oven is preheated to about 45° C. before the gloves are introduced. The oven has a temperature control mechanism to maintain a maximum temperature. In a preferred embodiment the maximum temperature is set at approximately 65° C. and the heating process lasts from about 35 to 40 minutes. The dehydration process provides an affiliation force so that Aloe Vera can remain associated with the glove surface for an extensive period of time.

Even distribution of Aloe Vera on the glove surface maximizes therapeutic treatment of the hand and minimizes contact between the skin and the glove's composite material. Stationary drying is not preferred because the Aloe Vera solution tends to flow in the direction of the force of gravity. In a preferred embodiment the heating oven has a device to tumble during the heating to make Aloe Vera distribute evenly on the glove surface and to form a uniform coating.

Afterward the gloves are cooled to room temperature. The gloves are then inverted so that the surface with the Aloe Vera faces inside.

What is claimed is:

1. A disposable examination glove comprising:
    a) only a single layer of a flexible material forming a cavity to receive a hand; and
    b) a quantity of dehydrated Aloe Vera on an inner surface of the layer of the flexible material, the Aloe Vera contacting the hand during donning of the disposable examination glove,
    wherein the aloe vera is attached to the flexible material by dipping the glove into a solution comprising aloe vera, removing the glove from said solution and subsequently heating the glove to form a layer of dehydrated aloe vera on the surface of the glove.

2. The disposable examination glove of claim 1 in which the layer of the flexible material is made of natural rubber latex.

3. The disposable examination glove of claim 1 in which the layer of the flexible material is made of acrylonitrile.

4. The disposable examination glove of claim 1 in which the Aloe Vera is attached to the flexible material through dehydration.

5. The disposable examination glove of claim 4 in which the Aloe Vera is evenly distributed on the flexible material.

6. The disposable examination glove of claim 1 in which the Aloe Vera forms a layer with thickness of about 0.01 mm.

7. The disposable examination glove of claim 1 in which the Aloe Vera forms a layer with a thickness that is about 1/16 of the thickness of the layer of the flexible material.

8. A method of manufacturing a disposable glove for protecting and soothing hands, comprising the steps of:
    a) mixing a quantity of water with Aloe Vera so as to dissolve the Aloe Vera and form a solution;
    b) arranging the glove inside out whereby an inner surface of the glove faces outward, wherein the inner surface is a surface of the glove that would face inward toward a hand while the glove is being worn on the hand;
    c) dipping the glove into the solution so that the inner surface is in contact with the solution;
    d) removing the glove out of the solution, wherein a portion of the solution is on the glove;

e) heating the glove with the portion of the solution to cause water in the portion of the solution to evaporate and form a substantially evenly distributed layer of dehydrated Aloe Vera on the surface of the glove;

f) cooling the glove to room temperature.

9. The method of manufacturing a glove of claim 8, further comprising the steps of:

a) pre-treating the glove by bringing the glove into an environment containing chlorine;

b) drying the gloves by heating, such that powders and proteins are removed, bacteria and viruses are killed, and the glove is ready for the manufacturing method set forth in claim 8.

10. The method of claim 8, wherein the solution has a concentration of about 15–30%.

11. The method of claim 8, wherein the heating step further comprises the steps of:

a) heating a drying machine to about 45° C. before the glove is introduced into the machine;

b) setting a maximum temperature at about 65° C.;

c) starting a tumbling mechanism that force gloves in the machine to tumble;

d) Keeping the heating and tumbling running for about 35 to 40 minutes.

12. A disposable glove manufactured according to claim 8.

* * * * *